United States Patent
Jiang et al.

(10) Patent No.: US 8,563,725 B2
(45) Date of Patent: Oct. 22, 2013

(54) PREPARATION OF SATURATED KETONE MORPHINAN COMPOUNDS HAVING LOW METAL CONTENT

(75) Inventors: Tao Jiang, Chesterfield, MO (US); Peter X. Wang, Creve Coeur, MO (US); David W. Berberich, St. Peters, MO (US)

(73) Assignee: Mallinckrodt LLC, Hazelwood, MO (US)

(*) Notice: Subject to any disclaimer, the term of this patent is extended or adjusted under 35 U.S.C. 154(b) by 293 days.

(21) Appl. No.: 13/093,892

(22) Filed: Apr. 26, 2011

(65) Prior Publication Data

US 2011/0269963 A1 Nov. 3, 2011

Related U.S. Application Data

(60) Provisional application No. 61/329,125, filed on Apr. 29, 2010.

(51) Int. Cl.
*C07D 489/02* (2006.01)
*C07D 489/08* (2006.01)

(52) U.S. Cl.
USPC .............................................. 546/45; 546/44

(58) Field of Classification Search
USPC ...................................................... 546/45, 44
See application file for complete search history.

(56) References Cited

U.S. PATENT DOCUMENTS

| 6,887,999 | B1 | 5/2005 | Likhotvorik |
| 6,946,556 | B1 | 9/2005 | Likhotvorik et al. |
| 7,321,038 | B2 * | 1/2008 | Wang et al. ..................... 546/45 |

FOREIGN PATENT DOCUMENTS

| WO | 2005/047291 | A1 | 5/2005 |
| WO | 2005/100361 | A1 | 10/2005 |
| WO | 2006/052710 | A1 | 5/2006 |

* cited by examiner

*Primary Examiner* — Charanjit Aulakh

(57) ABSTRACT

The present invention provides processes for the preparation of saturated ketone morphinan compounds from a morphinan comprising an allyl alcohol ring moiety, wherein the final product has a low metal content. In particular, the invention provides processes that utilize isomerization reactions catalyzed by transition metal catalysts and the subsequent removal of the transition metal using metal scavengers.

16 Claims, No Drawings

PREPARATION OF SATURATED KETONE MORPHINAN COMPOUNDS HAVING LOW METAL CONTENT

CROSS REFERENCE TO RELATED APPLICATIONS

This application claims the benefit of U.S. Provisional Application No. 61/329,125 filed Apr. 29, 2010, which is incorporated herein in its entirety.

FIELD OF THE INVENTION

The present invention generally relates to the preparation of saturated ketone morphinan compounds, wherein the compounds are substantially metal-free. In particular, the invention relates to the use of a transition metal catalyst to convert a morphinan comprising an allyl alcohol ring moiety into a morphinan comprising a saturated ketone ring moiety and the subsequent removal of the transition metal catalyst using a metal scavenger.

BACKGROUND OF THE INVENTION

Hydromorphone and hydrocodone are opioid analgesic drugs available in the market and both are generally used for relief of moderate to severe pain in patients where an opioid analgesic is appropriate. Hydrocodone is the most frequently prescribed opiate in the United States. Although hydromorphone is two to three times more potent than hydrocodone, it is also at least two to four times more expensive than hydrocodone. The higher cost of hydromorphone is due to the difficulty of its production. Despite this, however, prescriptions for hydromorphone products increased from about 0.47 million in 1998 to about 1.83 million in 2006. The aggregate production quota for hydromorphone as established by DEA increased from 766 kilograms in 1998 to 3,300 kilograms in 2006.

One of the current methods for the production of hydromorphone or hydrocodone involves a two-step oxidation/reduction route from morphine or codeine, respectively. This method, however, is expensive, low yielding, and forms impurities that are difficult to remove. Another production method involves the isomerization of morphine to hydromorphone in the presence of a late transition metal and a metal chloride. This method is also low yielding because significant amounts of impurities are generated. Moreover, the products have high levels of metal contamination. Thus, there is a need for new processes for producing hydromorphone or hydrocodone at lower costs, with higher yields and higher purity to meet the increasing demand for these analgesics.

SUMMARY OF THE INVENTION

Among the various aspects of the present invention is the provision of a process for preparing a morphinan comprising a saturated ketone ring moiety, wherein the morphinan comprising the saturated ketone ring moiety is substantially metal-free. The process comprises contacting a morphinan comprising an allyl alcohol ring moiety with a transition metal catalyst such that the allyl alcohol ring moiety is catalytically isomerized to the saturated ketone ring moiety. The process further comprises contacting the isomerization reaction product with a metal scavenger, wherein the metal scavenger binds the transition metal catalyst, thereby yielding the morphinan comprising the saturated ketone ring moiety that is substantially metal-free.

Another aspect of the invention encompasses a process for preparing a compound comprising Formula (II), wherein the compound comprising Formula (II) is substantially metal-free. The process comprises contacting a compound comprising Formula (I) with a transition metal catalyst to form a reaction product comprising the compound comprising Formula (II). The process further comprises contacting the reaction product comprising the compound comprising Formula (II) with a metal scavenger, wherein the metal scavenger binds the transition metal catalyst, thereby yielding the substantially metal-free compound comprising Formula (II). The compounds comprising Formulas (I) and (II) have the following structures:

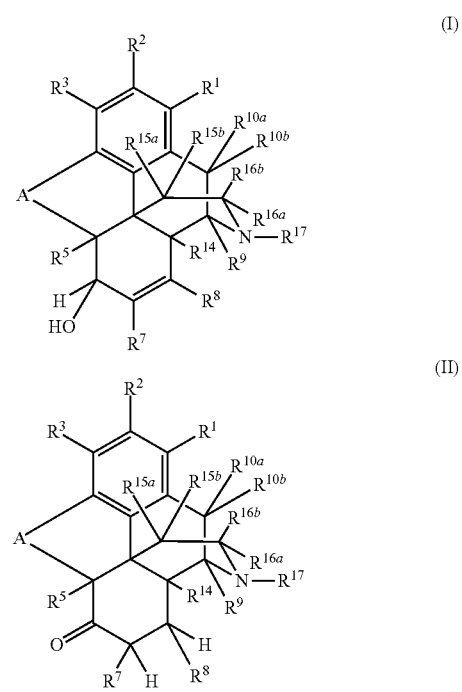

wherein:

A is oxygen or sulfur;

$R^1$, $R^2$, and $R^3$ are independently chosen from hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently chosen from hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}NR$^{1613}$;

$R^{1611}$, $R^{1612}$, and $R^{1613}$ are independently chosen from hydrocarbyl, and substituted hydrocarbyl; and one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof.

Other aspects and features of the invention are detailed below.

DETAILED DESCRIPTION OF THE INVENTION

The present invention provides an efficient one-pot synthesis process for the preparation of a saturated ketone morphinan that has a low metal content. The process comprises catalyzing the isomerization of an allyl alcohol morphinan to a saturated ketone morphinan with a transition metal catalyst, followed by removal of the transition metal catalyst using a metal scavenger. The resultant saturated ketone morphinan generally has a metal content of less than about 100 ppm, less than about 20 ppm, or even less than about 5 ppm. Thus, the present invention provides cost effective processes for the preparation of saturated ketone morphinans of high purity and excellent yields. In exemplary embodiments, the processes of the invention may be used to catalytically convert morphine or codeine into hydromorphone or hydrocodone, respectively, wherein the hydromorphone or hydrocodone product is substantially metal-free.

(I) Processes for Preparing Saturated Keto Morphinans Having a Low Metal Content One aspect of the present invention provides a process for converting a morphinan comprising an allyl alcohol ring moiety to a morphinan comprising a saturated ketone ring moiety, wherein the morphinan comprising the saturated ketone ring moiety is substantially metal free. The process comprises contacting the morphinan comprising the allyl alcohol ring moiety with a transition metal catalyst, wherein the allyl alcohol ring moiety undergoes an isomerization reaction thereby forming the saturated ketone ring moiety. The process further comprises contacting the isomerization reaction product with a metal scavenger, wherein the metal scavenger binds the transition metal catalyst, thereby forming the substantially metal-free saturated ketone morphinan.

(II) Processes for Preparing a Compound Comprising Formula (II) Having a Low Metal Content Another aspect of the present invention encompasses a process for preparing a compound comprising Formula (II), wherein the compound comprising Formula (II) is substantially metal-free. The process comprises Step A in which a compound comprising Formula (I) is contacted with a transition metal catalyst, wherein the compound comprising Formula (I) undergoes a double bond isomerization to form a reaction product comprising the compound comprising Formula (II). The process further comprises Step B in which the reaction product comprising the compound comprising Formula (II) is contacted with a metal scavenger, wherein the metal scavenger binds the transition metal catalyst, thereby forming the substantially metal-free compound comprising Formula (II). For the purposes of illustration, Reaction Scheme 1 depicts preparation of the compound comprising Formula (II) according to this aspect of the invention:

Reaction Scheme 1:

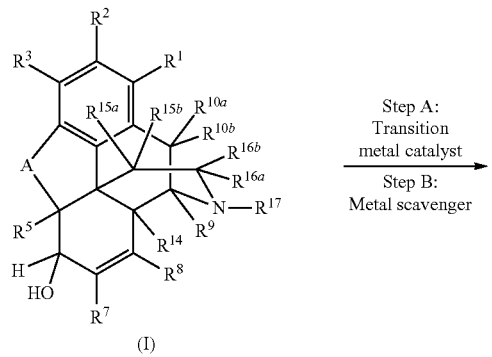

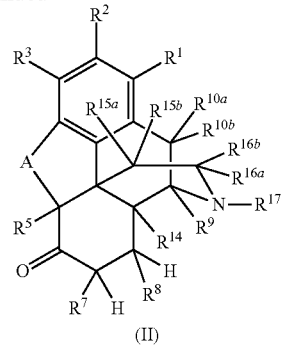

wherein:
A is oxygen or sulfur;
$R^1$, $R^2$, and $R^3$ are independently chosen from hydrogen, halogen, hydroxy, protected hydroxy, {—}SH, {—}$SR^{1611}$, {—}$OR^{1611}$, and {—}$NR^{1611}R^{1612}$, hydrocarbyl, and substituted hydrocarbyl;
$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently chosen from hydrogen, halogen, hydroxy, {—}SH, {—}$SR^{1511}$, {—}$OR^{1611}$, and {—}$NR^{1611}R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}$NR^{1613}$;
$R^{1611}$, $R^{1612}$, and $R^{1613}$ are independently chosen from hydrocarbyl, and substituted hydrocarbyl; and
one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof.

In one embodiment, A is oxygen. In another embodiment, each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen. In still another embodiment, $R^3$ is selected from the group consisting of hydroxy, protected hydroxy, alkyloxy, and acyloxy. In yet another embodiment, $R^{17}$ is selected from the group consisting of hydrogen, alkyl, cycloalkyl, cycloalkylmethyl, allyl, and aryl. In a further embodiment, $R^{14}$ is hydrogen or hydroxy. In still another embodiment, A is oxygen; each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen; $R^3$ is hydroxy or methoxy; $R^{14}$ is hydrogen; and $R^{17}$ is methyl.

(a) Step A—Reaction Mixture

Step A of the process comprises contacting the compound comprising Formula (I) with a transition metal catalyst such that the allyl alcohol ring moiety of the compound comprising Formula (I) is catalytically isomerized to the saturated ketone ring moiety of the compound comprising Formula (II). The process commences with the formation of a reaction mixture comprising the substrate, i.e., the compound comprising Formula (I), the transition metal catalyst, and a solvent.

(i) Transition Metal Catalyst

A wide variety of transition metal catalysts may be used in the process to catalyze the isomerization reaction. As used herein, the term "transition metal catalyst" refers to a transition metal element, a transition metal salt, or a transition metal complex. In general, the transition metal may be any transition metal. In some embodiments, the transition metal may be iridium, nickel, osmium, palladium, platinum, rhodium, or ruthenium. A skilled artisan appreciates that the oxidation state of the transition metal may vary.

In some embodiments, the transition metal catalyst may be the transition metal element itself. For example, the transition metal element may be a powder or a sponge, such as, e.g., ruthenium powder, rhodium powder, ruthenium sponge, rhodium sponge, palladium sponge, and so forth. Alternatively, the transition metal element may be rhodium black, ruthenium black, palladium black, etc. In still other embodiments, the transition metal element may be immobilized on a solid surface or support. Suitable examples include, but are not limited to, ruthenium on carbon, rhodium on carbon, palladium on carbon, ruthenium on alumina, rhodium on alumina, platinum on alumina, palladium on alumina, rhodium on silica, palladium on silica, palladium on charcoal, palladium on pumice, and so forth.

In other embodiments, the transition metal catalyst may be a transition metal salt. Non-limiting examples of suitable salts include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, trifluoromethanesulfonates, trimethylacetates, tosylates, and combinations thereof. Non-limiting examples of suitable transition metal salts include $RuCl_3$, $RuBr_3$, $Ru(CF_3SO_3)_2$, $Ru_2(SO_4)_3$, $Ru(NO_3)_3$, $Ru(OAc)_3$, $PdCl_2$, $Pd(OAc)_2$, $RhCl_3$, $RhBr_3$, $Rh_2(SO_4)_3$, $(Rh(CO_2)Cl)_2$, $Rh_2(SO_4)_3$, $Rh_2(OAC)_4$, $IrCl_3$, and $OsCl_3$. The transition metal salt may be soluble (i.e., homogeneous). Alternatively, the transition metal salt may be immobilized on a solid support (i.e., heterogeneous). The transition metal salt may be immobilized on the solid support via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

In further embodiments, the transition metal catalyst may be a transition metal complex. In general, a transition metal complex comprises the transition metal and 4, 5, or 6 coordinate species with oxidation states ranging from 0 to 8. The complexes may be ionic, or the complexes may comprise covalently bound ligands and counter ions. Alternatively, the complexes may comprise a mixture of ionic and covalent bonds between the metal, ligand(s), and/or counter ion(s). The ligand may be monodentate or polydentate. Non-limiting examples of suitable ligands include arene ligands, olefin ligands, alkyne ligands, heterocycloalkyl ligands, heteroaryl ligands, alkyl ligands, cyclopentadienyl ligands, hydride ligands, amine ligands, carbonyl ligands, nitrogen donor ligands, phosphorous donor ligands, oxygen donor ligands, and so forth. The ligand may also be a solvent such as, e.g., DMSO, methanol, methylene chloride, tetrahydrofuran, acetone, ethanol, pryridine, or a tetraalkylammonia compound. Suitable counter ions include, but are not limited to, halides, $BF_4$, $PF_6$, $ClO_4$, $CHO_2$, $CF_3SO_3$, $CH_3CO_2$, $ArCO_2$, $CH_3SO_3$, p-tolyl$SO_3$, $HSO_4$, $H_2PO_4$, and hydrocarbyl anions. Numerous transition metal complexes are detailed in "Transposition of Allylic Alcohols into Carbonyl Compounds Mediated by Transition Metal Complexes" by Uma et al., Chem. Rev. 103: 27-51 (2003).

In some embodiments, the transition metal complex may be a bis-allyl transition metal complex. Non-limiting examples of suitable bis-allyl transition metal complexes include bis-$\eta^3$-bonded ruthenium complexes such as, e.g., $\{Ru(\eta^3:\eta^3-C_{10}H_{16})(\mu-Cl)Cl\}_2$, $Ru(\eta^3:\eta^2:\eta^3-C_{12}H_{18})Cl_2$, $\{Ru(\eta^3:\eta^3-C_{12}H_{20})(\mu-Cl)Cl\}_2$, and bis($\eta^3$-allyl)-ruthenium-(1,5-cyclooactadiene).

In other embodiments, the transition metal catalyst may be a complex comprising the transition metal and a tertiary phosphite, a tertiary phosphine, or a tertiary phosphine halide as detailed in U.S. Pat. Nos. 7,321,038, 7,399,858, and 7,323,565, each of which is incorporated herein in its entirety. Non-limiting examples of phosphine containing complexes include $(phosphine)_xPdCl_2$, $(PPh_3)_4Pd$, $RuCl_2(PPh_3)_3$, $RuCl_2(PPh_3)_4$, $RuH_2(PPh_3)_4$, and $RhCl(PPh_3)_3$. In yet another embodiment, transition metal catalyst may be a complex comprising the transition metal and an amine phosphine complex as described in U.S. Pat. No. 7,399,859, which is incorporated herein in its entirety.

The transition metal complex may be soluble (i.e., homogeneous). Alternatively, the transition metal complex may be immobilized on a solid support (i.e., heterogeneous). The transition metal complex may be immobilized on the solid support via noncovalent or covalent bonds. Examples of suitable solid supports are presented above.

The weight ratio of the compound comprising Formula (I) to the transition metal catalyst can and will vary. In general, the weight ratio of the compound comprising Formula (I) to the transition metal catalyst may range from about 1:0.0001 to about 1:0.1. In various embodiments, the weight ratio of the compound comprising Formula (I) to the transition metal catalyst may range from about 1:0.0001 to about 1:0.001, from about 1:0.001 to about 1:0.01, or from about 1:0.01 to about 1:0.1. In one embodiment, the weight ratio of the compound comprising Formula (I) to the transition metal catalyst may range from about 1:0.001 to about 1:0.05. In another embodiment, the weight ratio of the compound comprising Formula (I) the transition metal catalyst may range form about 1:0.001 to about 1:0.01.

(ii) Solvent

The reaction mixture of step A also comprises a solvent. The solvent may be a protic solvent, an aprotic solvent, or combinations thereof. Non-limiting examples of suitable protic solvents include a C1-C4 alcohol (such as, e.g., methanol, ethanol, isopropanol, n-propanol, isobutanol, n-butanol, s-butanol, t-butanol), formic acid, acetic acid, water, and combinations thereof. Examples of suitable aprotic solvents include, but are not limited to, acetone, acetonitrile, diethoxymethane, N,N-dimethylformamide (DMF), N,N-dimethylpropionamide, 1,3-dimethyl-3,4,5,6-tetrahydro-2 (1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), 1,4-dioxane, N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. In some embodiments, the solvent may be a protic solvent. In one iteration, the solvent may be mixture of an alcohol and water. For example, the solvent may be a mixture of ethanol and water. In general, the volume ratio of ethanol to water will range from about 1:10 to about 10:1.

The weight ratio of the solvent to the compound comprising Formula (I) can and will vary. Typically, the weight ratio of the solvent to the compound comprising Formula (I) may range from about 0.5:1 to about 20:1. In various embodiments, the weight ratio of the solvent to the compound comprising Formula (I) may range from about 0.5:1 to about 2:1, from about 2:1 to about 5:1, from about 5:1 to about 10:1, or from about 10:1 to about 20:1. In one embodiment, the weight ratio of the solvent to the compound comprising Formula (I) may range from about 1:1 to about 10:1. In another embodiment, the weight ratio of the solvent to the compound comprising Formula (I) may range from about 2:1 to about 6:1.

The pH of the reaction mixture may be adjusted to optimize activity of the transition metal catalyst. In general, the optimal pH will vary depending upon the nature of the transition metal catalyst. A person of skill in the art will know how to determine the optimal pH level for the transition metal catalyst of interest.

(b) Step A—Reaction Conditions

The temperature of the reaction may vary. In general, the reaction is allowed to proceed at a temperature that may range from about 10° to about 120° C. In some embodiments, the temperature of the reaction may range from about 45° to about 100° C. In further embodiments the temperature may range from about 65° to about 90° C. In one embodiment, the temperature of the reaction may range from about 75° to about 85° C. In another embodiment, the temperature of the reaction may range from about 80° to about 100° C. Generally, the reaction will be conducted under ambient pressure, and under an inert atmosphere (e.g., nitrogen or argon).

The duration of the reaction can and will vary. For example, the reaction may be allowed to proceed for about 1 hour, 2 hours, 3 hours, 4 hours, 5 hours, 6 hours, 8 hours, 10 hours, 12 hours, 14 hours, 16 hours, 18 hours, 20 hours, 22 hours, or 24 hours. Typically, however, the reaction is allowed to proceed for a sufficient period of time until the reaction is complete, as determined by any method known to one skilled in the art, such as chromatography (e.g., HPLC). In this context, a "completed reaction" generally means that the reaction product mixture contains a significantly diminished amount of the compound comprising Formula (I) and a significantly increased amount of the compound comprising Formula (II) compared to the amounts of each present at the beginning of the process. Typically, the amount of the compound comprising Formula (I) remaining in the reaction mixture may be less than about 3%, less than about 1%, and preferably less than about 0.5%.

Upon completion of the reaction, the reaction product mixture may be cooled. Typically, the reaction product comprising the compound comprising Formula (II) will be used directly for step B, as detailed below. The entire two-step process, therefore, comprises a one-pot synthesis.

(c) Step B—Reaction Mixture

Step B of the process comprises contacting the reaction product comprising the compound comprising Formula (II) with a metal scavenger. During this step of the process, the metal scavenger binds the transition metal catalyst, thereby forming the substantially metal-free compound comprising Formula (II).

(i) Metal Scavenger

A variety of metal scavengers are suitable for use in the process of the invention. The choice of metal scavenger depends upon the transition metal present in the reaction product of Step A, the oxidation state or range of oxidation states of the metal, the nature of the compound comprising Formula (II), the solvent present in the reaction product, and the pH of the mixture. The nature of the functional group of the metal scavenger can and will vary. Non-limiting examples of suitable functional groups include acetyl, amide, amine, amino, guanidine, imidazole, imine, mercaptophenyl, phosphoric acid, trimercaptotriazine, triamine, thiol, thiourea, and combinations thereof. In one embodiment, the metal scavenger comprises a thiol functional group.

In some embodiments, the metal scavenger may be attached to a solid support. The attachment may be covalent or non-covalent. In some embodiments, the solid support may be an inorganic material. Suitable inorganic materials include, without limit, silicas, alumina, titania, carbondium, zirconia, activated charcoal, zeolites, clays, polymers, ceramics, and activated carbon, Suitable silicas include silicon dioxide, amorphous silica, and microporous or mesoporous silicas. In other embodiments, the solid support may be an organic polymer. Non-limiting examples of polymers include agarose, cellulose, nitrocellulose, methyl cellulose, polyacrylic, polyacrylamide, polyacrylonitrile, polyimide, polyether, polyester, polyethylene, polystyrene, polysulfone, polyvinyl chloride, polyvinylidene, methacrylate copolymer, and polystyrene-vinyl chloride copolymer.

The amount of metal scavenger added to the reaction product can and will vary. In general, the weight ratio of the starting substrate, i.e., the compound comprising Formula (I), to the metal scavenger will range from about 1:0.005 to about 1:0.5. In some embodiments, the weight ratio of the compound comprising Formula (I) to the metal scavenger may range from about 1:0.005 to about 1:0.015, from about 1:0.015 to about 1:0.05, from about 1:0.05 to about 1:0.15, or from about 1:0.15 to about 1:0.5. In some embodiments, the weight ratio of the compound comprising Formula (I) to the metal scavenger may range from about 1:0.02 to about 1:0.1. In one embodiment, the weight ratio of the compound comprising Formula (I) to the metal scavenger may be about 1:0.05.

(ii) Solvent

Step B of the process typically is conducted in the presence of a solvent. The solvent may be a protic solvent, an aprotic solvent, or combinations thereof. Suitable protic and aprotic solvents are presented above in section (II)(a)(ii). In one embodiment, the solvent may be mixture of an alcohol and water. For example, the solvent may be a mixture of ethanol and water. In general, the volume ratio of ethanol to water will range from about 1:10 to about 10:1. Suitable concentrations of the solvent are detailed above in (II)(a)(ii).

In general, the reaction of step B is conducted in an acidic environment. That is, the pH of the reaction mixture may range from about 0 to about 7. In some embodiments, the pH of the mixture may range from about 1 to 2, from about 2 to 3, from about 3 to 4, from about 4 to 5, from about 5 to 6, or from about 6 to 7. In one embodiment, the pH of the reaction mixture may be less than about 2.5. In one embodiment, the pH of the reaction mixture may range from about 2.5 to about 5.5. In a further embodiment, the pH of the reaction mixture may be adjusted to about pH 2.5 and, then after a period of reaction, the pH may be adjusted to about pH 4 to 6. Those of skill in the art will know how to adjust the pH of the reaction product mixture to attain the desired pH value.

(d) Step B—Reaction Conditions

Typically, Step B of the process is allowed to proceed at a temperature that may range from about 10° to about 120° C. In some embodiments, the temperature of the reaction may range from about 50° to about 110° C. In other embodiments, the temperature of the reaction may range from about 60° to about 105° C. In further embodiments, the temperature of the reaction may range from about 80° to about 103° C. The reaction typically is conducted under ambient pressure and an inert atmosphere (i.e., nitrogen or argon).

The duration of the reaction can and will vary. Typically, the reaction may proceed for a period of time ranging from about 3 hours to about 48 hours. In some embodiments, the duration of the reaction may range from about 3-6 hours, from about 6-12 hours, from about 12-24 hours, or from about 24-48 hours. Typically, the reaction is allowed to proceed until substantially all of the transition metal is bound or complexed with the metal scavenger, thereby forming a metal scavenger/transition metal complex. The completeness of the reaction may be monitored by techniques known to those of skill in the art. Upon completion of the reaction, the reaction mixture may be cooled and the substantially metal-free compound comprising Formula (II) may be isolated using techniques know to those of skill in the art.

(e) Optional Separation Step

In some embodiments, the substantially metal-free compound comprising Formula (II) may be separated from the metal scavenger/transition metal complex. In some embodiments, the separation may comprise a filtration step. For this, charcoal and/or a filtration aid may be added to the reaction mixture to facilitate filtration. In other embodiment, the separation may comprise a centrifugation step, wherein the supernatant comprising the compound of Formula (II) may be removed from the pellet comprising the metal scavenger/transition metal complex. In yet another embodiment, the separation may be performed by allowing the metal scavenger/transition metal complex to settle by gravity, wherein the supernatant comprising the compound of Formula (II) may be removed from the settled metal scavenger/transition metal complex.

Upon separation of the metal scavenger/transition metal complex from the substantially metal-free compound comprising Formula (II), the compound comprising Formula (II) may be further isolated using means well known to those of skill in the art. Suitable means include precipitation, filtration, distillation, phase extraction, crystallization, etc. The final product may be washed and dried, and analyzed by HPLC, HPLC, MS, NMR, IR, or TGA. The final product generally will have a coloration that is white or off-white.

The yield of the compound comprising Formula (II) can and will vary. Typically, the molar yield of the compound comprising Formula (II) will be at least about 60%. In some embodiments, the molar yield of the compound comprising Formula (II) may be at least about 65%, or at least about 70%. In other embodiments, the molar yield of the compound comprising Formula (II) may be at least about 75%, at least about 80%, or at least about 85%. In still further embodiments, the molar yield of the compound comprising Formula (II) may be at least about 90%, at least about 95%, at least 97%, or at least about 99%.

Upon completion of the process, the compound comprising Formula (II) is substantially metal free. In one embodiment, the compound comprising Formula (II) may have a metal content of less than about 100 ppm. In another embodiment, the compound comprising Formula (II) may have a metal content of less than about 50 ppm. In still another embodiment, the compound comprising Formula (II) may have a metal content of less than about 10 ppm. In a further embodiment, the compound comprising Formula (II) may have a metal content of less than about 5 ppm. In an additional embodiment, the compound comprising Formula (II) may have a metal content of less than about 2 ppm.

The compound comprising Formula (II) prepared by the process of the invention may be an end product itself, or may be further derivatized in one or more steps to yield further intermediates or end products. In some embodiments, the compound comprising Formula (II) may be converted into a pharmaceutically acceptable salt using techniques well known to those of skill in the art. Pharmaceutically acceptable salts include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpriopionate, phosphate, phthalate, propionate, pyruvate, salicylate, stearate, succinate, sulfate, tannate, tartrate, terephthalate, valerate, and the like.

(f) stereochemistry

The substrates and the products of the processes of the invention are morphinan compounds. For the purposes of discussion, the ring atoms of a morphinan compound are numbered as diagrammed below. Morphinan compounds have asymmetric centers. In particular, the core morphinan compound may have at least four chiral carbons (designated by asterisks); namely, C-5, C-13, C-14, and C-9.

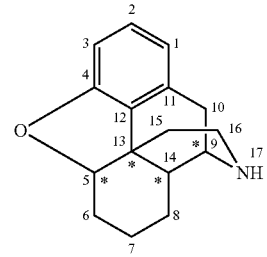

Any of the compounds comprising Formula (II) may have a (−) or (+) orientation with respect to the rotation of polarized light, depending upon whether the starting substrate, i.e., the compound comprising Formula (I), has (−) or (+) optical activity. More specifically, each chiral center has an R or an S configuration. In particular, the configuration of the chiral carbons C-5, C-13, C-14, and C-9 may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule, (III) Processes for Preparing a Compound Comprising Formula (IIa) Having a Low Metal Content A further aspect of the invention provides a process for preparing a compound comprising Formula (IIa) that is substantially metal-free. The process comprises Step A in which a compound comprising Formula (Ia) is contacted with a transition metal catalyst, wherein the compound comprising Formula (Ia) undergoes a double bond isomerization to form a reaction product comprising the compound comprising Formula (IIa). The process further comprises Step B in which the reaction product comprising the compound comprising Formula (IIa) is contacted with a metal scavenger, wherein the metal scavenger binds the transition metal catalyst, thereby forming the substantially metal-free compound comprising Formula (IIa). For the purposes of illustration, Reaction Scheme 2 depicts preparation of the compound comprising Formula (IIa) according to this aspect of the invention:

Reaction Scheme 2:

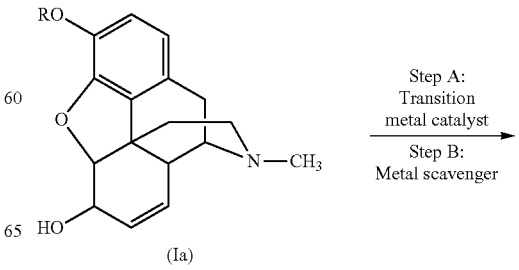

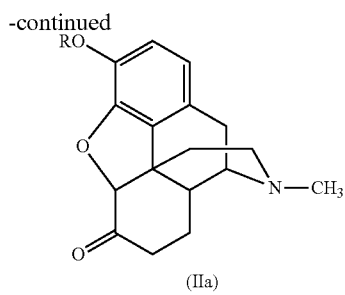

(IIa)

wherein:

R is hydrogen or methyl.

Steps A and B of the process are detailed above in sections (II)(a)(b) and (II)(c)(d), respectively. In one embodiment, the transition metal catalyst may be a bis(allyl)-ruthenium complex; the weight ratio of the compound comprising Formula (Ia) to the bis(allyl)-ruthenium complex may range from about 1:0.001 to about 1:0.05; step A of the process may be conducted in the presence of a protic solvent comprising ethanol and water; the weight ratio of the protic solvent to the compound comprising Formula (Ia) may be about 1:1 to about 10:1; the temperature of step A may range from about 65° C. to about 90° C.; the metal scavenger may comprise a thiol functional group and may be attached to a silica-based solid phase; the weight ratio of the compound comprising Formula (Ia) to the metal scavenger may range from about 1:0.02 to about 1:0.1; step B may be conducted in the presence of the same solvent used in step A but at a pH from about 2 to about 5.5; step B may be conducted at a temperature from about 60° C. to about 105° C.; the compound comprising Formula (IIa) may be separated from the metal scavenger by filtration after step B; the compound comprising Formula (IIa) may have a yield of at least about 80%; and the compound comprising Formula (IIa) may have a metal content of less than abut 50 ppm. In embodiments in which the optical activity of the compounds comprising Formulas (Ia) and (IIa) is (−), the configuration of C-5, C-13, C-14, and C-9, respectively, may be RSRR. In embodiments in which the optical activity of the compounds comprising Formulas (Ia) and (IIa) is (+), the configuration of C-5, C-13, C-14, and C-9, respectively, may be SRSS.

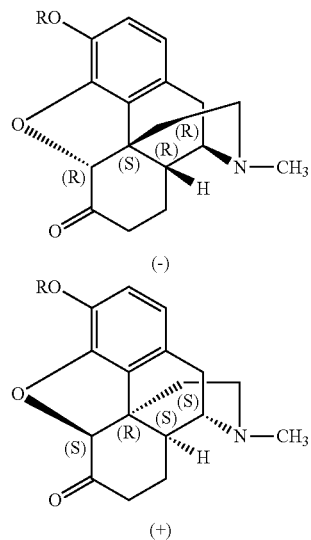

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), f-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Preparation of Hydromorphone from Morphine

Water (150 mL) and c-$H_2SO_4$ (30 g) were added to a flask. Morphine base (wet 127 g, containing 100 g dry base) was added with stirring. The reactor was flushed with nitrogen and kept under nitrogen throughout the isomerization reaction. Ethanol (50 mL) and ruthenium-isoprene-dimer (0.4 g) were added. The reaction mixture was heated to reflux for 3 h and then cooled down to 75° C. (HPLC indicated the reaction was complete).

To the above solution, 50% NaOH (19 g) was added. Thiol-beads (5.0 g, Thiol-SAMMS®, Steward Advanced Materials, Chattanooga, Tenn.) and water (100 mL) were added. After stirring for 15 min, the pH was checked and adjusted to 2.85 with either 50% NaOH or c-$H_2SO_4$. The mixture was heated to distill off about 65 mL of the solvents, and then the mixture was heated to reflux (100-102° C.) for 6 h. The mixture was cooled to 75° C., the pH was adjusted to 6.2, and then the mixture was heated to reflux for another 6 h. After the mixture was cooled to 75° C., charcoal (2.5 g) and filter aid (7.5 g) were added and the mixture was maintained at 75° C. for 1 hr. The mixture wan then filtered, and the solids on the filter were washed with hot water (2×50 mL, 75° C.).

To the combined filtrate and washes, HOAc (10 mL), EDTA (2.5 g) and L-Ascorbic acid (2.5 g) were added. The pH was adjusted to 5.3 with c-$NH_4OH$. The mixture was maintained at 75° C. for 2 h and then cooled to 50° C. c-$NH_4OH$ was added until pH was 7.2. The pH was further adjusted to 9 and the mixture was maintained at 50° C. for 30 min. Then the mixture was cooled to room temperature, the pH was adjusted 9.0, kept at room temperature for 2 h, and then filtered. The solids were washed with water (3×50 mL), and dried at 55-65° C. for 18 h to give 93 g of product as an off white/white solid. Ruthenium in the product was 2.5 ppm, as measured by ICP-MS.

Example 2

Preparation of Hydromorphone from Morphine

Morphine base (1.0 Kg, dry base) was added to a solution consisting of water (1.2 L) and 49% $H_2SO_4$ (0.60 Kg). EtOH (100%, 0.5 L) was added. The reactor was flushed with nitrogen for 10 min. Ru-Isopre-Dimer (0.004 Kg) was charged.

The mixture was heated with reflux (87-90° C.) for 3 hours and cooled down to 65° C. (HPLC indicated the reaction was complete).

The pH of the reaction mixture was adjusted with 25% NaOH to 2.4-2.8. Metal Scavenger (Thiol SAMMS, 0.05 Kg) and water (1.0 Kg) were charged. Volatiles were removed by distillation until the temperature of the reaction mixture reached 100° C. The mixture was heated with reflux for additional 12 h and cooled down to 65° C. Charcoal (0.025 Kg), filter aid (0.075 Kg) and water (2.0 L) were charged. The mixture was heated at 65° C. for 60 min. The solid waste was removed by filtration and washed with water (1.0 L).

EDTA (0.03 Kg), sodium bisulfite (0.005 Kg), acetic acid (0.3 Kg), and ammonium hydroxide (0.15 Kg, adjust pH to 4.0-4.7), acetonitrile (0.25 L), and ethanol (1.0 L) were added to the filtrate. It was heated at 75° C. for 2 h and cooled to 55° C. Ammonium hydroxide was added and the pH was adjusted to 8.7-9.2. The precipitated hydromorphone base was then collected by centrifugation or filtration, washed with water (3×0.5 L), dried at 55-65° C. The yield was 90-95%. The level of Ru in the product was 2 ppm, as measured by ICP-MS

What is claimed is:

1. A process for preparing a compound having Formula (II), wherein the compound having Formula (II) is substantially metal-free:

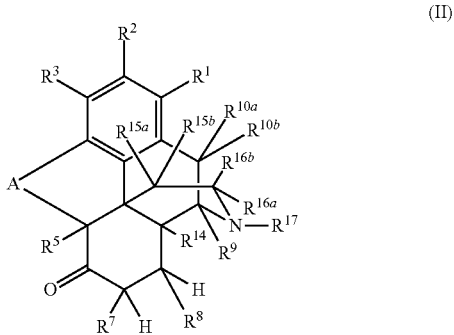

the process comprising:
a) contacting a compound having Formula (I) with a transition metal catalyst to form a reaction product comprising the compound having Formula (II); and
b) contacting the reaction product of step (a) with a metal scavenger such that the metal scavenger binds the transition metal catalyst, thereby yielding the substantially metal-free compound having Formula (II), the compound of Formula (I) being:

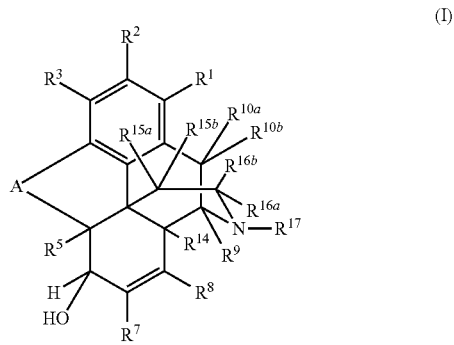

wherein:
A is oxygen;
$R^1$, $R^2$, and $R^3$ are independently chosen from hydrogen, halogen, hydroxy, protected hydroxy, {—}SH, {—}$SR^{1611}$, {—}$OR^{1611}$, and {—}$NR^{1611}R^{1612}$, hydrocarbyl, and substituted hydrocarbyl;
$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently chosen from hydrogen, halogen, hydroxy, {—}SH, {—}$SR^{1611}$, {—}$OR^{1611}$, and {—}$NR^{1611}R^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}$NR^{1613}$; and
$R^{1611}$, $R^{1612}$, an $R^{1613}$ are independently chosen from hydrocarbyl, and substituted hydrocarbyl.

2. The process of claim 1, wherein $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ are hydrogen; $R^3$ is chosen from hydroxy, protected hydroxy, alkyloxy, and acyloxy; $R^{14}$ is hydrogen or hydroxy; and $R^{17}$ is chosen from hydrogen, alkyl, cycloalkyl, cycloalkylmethyl, allyl, and aryl.

3. The process of claim 2, wherein $R^3$ is hydroxy or methyoxy; $R^{14}$ is hydrogen; and $R^{17}$ is methyl.

4. The process of claim 1, wherein the transition metal catalyst is chosen from a transition metal element, a transition metal salt, and a transition metal complex; and comprises a transition metal chosen from iridium, nickel, osmium, palladium, platinum, rhodium, and ruthenium.

5. The process of claim 4, wherein the transition metal salt comprises an anion chosen from an acetate, an acetyacetonate, an alkoxide, a butyrate, a carbonyl, a dioxide, a halide, a hexonate, a hydride, a mesylate, an octanate, a nitrate, a nitrosyl halide, a nitrosyl nitrate, a sulfate, a sulfide, a sulfonate, a phosphate, a trifluoromethanesulfonate, a trimethylacetate, a tosylate, and combinations thereof.

6. The process of claim 4, wherein the transition metal complex is chosen from a bis(allyl)-ruthenium complex selected from $\{Ru(\eta^3{:}\eta^3{-}C_{10}H_{16})(\mu{-}Cl)Cl\}_2$, $Ru(\eta^3{:}\eta^2{:}\eta^3{-}C_{12}H_{18})Cl_2$, and $\{Ru(\eta^3{:}\eta^3{-}C_{12}H_{20})(\mu{-}Cl)Cl\}_2$; and a phosphine complex selected form $(phosphine)_xPdCl_2$, $(PPh_3)_4Pd$, $RuCl_2(PPh_3)_3$, $RuCl_2(PPh_3)_4$, $RuH_2(PPh_3)_4$, and $RhCl(PPh_3)_3$.

7. The process of claim 1, wherein the weight ratio of the compound having Formula (I) to the transition metal catalyst is from about 1:0.0001 to about 1:0.1; and the weight ratio of the compound having Formula (I) to the metal scavenger is from about 1:0.005 to about 1:0.5.

8. The process of claim 1, wherein the metal scavenger comprises a functional group chosen from acetyl, amide, amine, amino, guanidine, imidazole, imine, mercaptophenyl, phosphonic acid, trimercaptotriazine, triamine, thiol, thiourea, and combinations thereof.

9. The process of claim 1, wherein steps (a) and (b) are conducted in the presence of a protic or an aprotic solvent; steps (a) and (b) are conducted at a temperature from about 10° C. to about 120° C.; and step (b) is conducted at a pH from about 0 to about 7.

10. The process of claim 1, wherein the process is a one-pot synthesis.

11. The process of claim 1, wherein the substantially metal-free compound of Formula (II) has a metal content of less than about 100 ppm.

12. The process of claim 1, wherein the optical activity of the compounds having Formulas (I) and (II) is (−) or (+), and the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

13. The process of claim 1, wherein the process is a one-pot synthesis; the transition metal catalyst is chosen from a transition metal element, a transition metal salt, and a transition metal complex; the metal of the transition metal catalyst is chosen from iridium, nickel, osmium, palladium, platinum, rhodium, and ruthenium; the weight ratio of the compound having Formula (I) to the transition metal catalyst is from about 1:0.0001 to about 1:0.1; the metal scavenger comprises a functional group chosen from acetyl, amide, amine, amino, guanidine, imidazole, imine, mercaptophenyl, phosphonic acid, trimercaptotriazine, triamine, thiol, thiourea, and combinations thereof; the weight ratio of the compound having Formula (I) to the metal scavenger is from about 1:0.005 to about 1:0.5; steps (a) and (b) are conducted in the presence of a protic solvent and at a temperature from about 10° C. to about 120° C.; the weight ratio of the protic solvent to the compound having Formula (I) is from about 0.5:1 to about 20:1; step (b) of the process is conducted at a pH from about 0 to about 7; the compound having Formula (II) is separated from the metal scavenger by filtration after step (b); the compound having Formula (II) has a yield of at least about 60%; and the compound having Formula (II) has a metal content of less than about 100 ppm.

14. The process of claim 13, wherein the optical activity of the compounds having Formulas (I) and (II) is (−) or (+), and the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

15. The process of claim 3, wherein the process is a one-pot synthesis; the transition metal catalyst is a bis(allyl)-ruthenium complex; the weight ratio of the compound having Formula (I) to the bis(allyl)-ruthenium complex is from about 1:0.001 to about 1:0.05; step (a) of the process is conducted in the presence of a protic solvent comprising ethanol and water and at a temperature from about 65° C. to about 90° C.; the weight ratio of the protic solvent to the compound having Formula (I) is about 1:1 to about 10:1; the metal scavenger has a thiol functional group and is attached to a silica-based solid phase; the weight ratio of the compound having Formula (I) to the metal scavenger is about 1:0.02 to about 1:0.1; step (b) of the process is conducted in the presence of a protic solvent comprising ethanol and water, at a pH from about 2 to about 3, and at a temperature from about 60° C. to about 105° C.; the compound having Formula (II) is separated from the metal scavenger by filtration after step (b); the compound having Formula (II) has a yield of at least about 80%; and the compound having Formula (II) has a metal content of less than about 50 ppm.

16. The process of claim 15, wherein the optical activity of the compounds having Formulas (I) and (II) is (−) or (+), and the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

\* \* \* \* \*